United States Patent [19]

Takeda et al.

[11] 3,932,429
[45] Jan. 13, 1976

[54] NOVEL AZABICYCLO OCTANE DERIVATIVE AND PROCESS FOR PREPARING SAME

[75] Inventors: Mikio Takeda, Urawa; Hirozumi Inoue, Kawaguichi; Goro Hayashi, Toyonaka; Seiichi Nurimoto, Toyonaka, all of Japan

[73] Assignee: Tanabe Seiyaku Co., Ltd, Osaka, Japan

[22] Filed: July 10, 1974

[21] Appl. No.: 486,988

[30] Foreign Application Priority Data

| July 14, 1973 | Japan | 48-79570 |
| July 14, 1973 | Japan | 48-79571 |
| July 14, 1973 | Japan | 48-79572 |
| July 23, 1973 | Japan | 48-82871 |
| July 23, 1973 | Japan | 48-82872 |
| Mar. 29, 1974 | Japan | 49-36055 |
| July 29, 1973 | Japan | 48-36056 |
| May 20, 1974 | Japan | 49-56888 |
| May 20, 1974 | Japan | 49-56889 |
| May 20, 1974 | Japan | 49-59126 |
| May 24, 1974 | Japan | 49-59129 |

[52] U.S. Cl.... 260/295.5 B; 260/326.32; 260/326.43; 260/326.5 B; 260/326.8; 260/326.87; 424/266; 424/274
[51] Int. Cl.² ............ C07D 451/02; C07D 401/06; C07D 209/02
[58] Field of Search... 260/295.5 B, 326.32, 326.43, 260/326.5 B, 326.8, 326.87

[56] References Cited
UNITED STATES PATENTS
3,600,400    8/1971    Schenker .......................... 260/326.8
FOREIGN PATENTS OR APPLICATIONS
952,137    3/1964    United Kingdom............ 260/326.32

OTHER PUBLICATIONS
Chemical Abstracts Vol. 76:14312j (1972).

*Primary Examiner*—Donald B. Moyer
*Attorney, Agent, or Firm*—Jordan B. Bierman; Linda G. Bierman; Kenneth J. Stempler

[57] ABSTRACT

A compound of the formula:

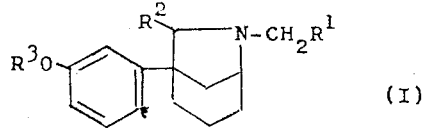

wherein $R^1$ is hydrogen, phenyl, alkyl of one to five carbon atoms, cycloalkyl of three to four carbon atoms, or alkyl of one to five carbon atoms having a substituent selected from the group consisting of phenyl, benzoyl and 4-fluorobenzoyl, $R^2$ is hydrogen or alkyl of one to three carbon atoms, and $R^3$ is hydrogen, alkanoyl of two to six carbon atoms, benzoyl or nicotinoyl is disclosed. Several methods for preparing the compound (I) is also disclosed. The compound (I) and a pharmaceutically acceptable acid addition salt thereof are useful as analgesic agents.

24 Claims, No Drawings

NOVEL AZABICYCLO OCTANE DERIVATIVE AND PROCESS FOR PREPARING SAME

This invention relates to a novel 1-phenyl-6-azabicyclo [3,2,1]octane derivative and a process for preparing same. More particularly, it relates to the compound of the formula:

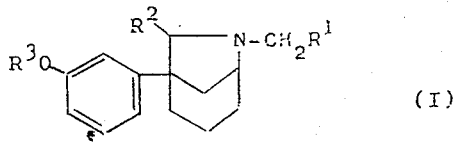

(I)

wherein $R^1$ is hydrogen, phenyl, alkyl of one to five carbon atoms, cycloalkyl of three to four carbon atoms, or alkyl of one to five carbon atoms having a substituent selected from the group consisting of phenyl, benzoyl and 4-fluorobenzoyl; $R^2$ is hydrogen or alkyl of one to three carbon atoms; and $R^3$ is hydrogen, alkanoyl of two to six carbon atoms, benzoyl or nicotinoyl pharmaceutically acceptable acid addition salts thereof are also contemplated as part of the invention.

It has been found that the compound (I) of the present invention is useful as an analgesic agent. The analgesic activity of the compound (I) is about 2 times or more as strong as that of codein. For example, when a one % acetic acid solution is injected intraperitoneally to mice at the dose of 10 mg/kg after subcutaneous injection of a test compound and the number of writhings per mouse is counted for 5 minutes starting at 10 minutes after injection of acetic acid, the analgesic activity(=$ED_{50}$) of 1-(3-hydroxyphenyl)-6,7-dimethyl-6-azabicyclo[3,2,1]octane hydrobromide which would produce a 50% reduction in acetic acid-induced writhings is 4.5 mg/kg. When examined under the same condition as above, the analgesic activity(=$ED_{50}$) of 1-(3-hydroxyphenyl)-6-n-amyl-7-methyl-6-azabicyclo[3,2,1]octane hydrochloride, 1-(3-hydroxyphenyl)-6-n-hexyl-7-methyl-6-azabicyclo[3,2,1]octane hydrochloride, 1-(3-hydroxyphenyl)-6-cyclopropylmethyl-7-methyl-6-azabicyclo[3,2,1]octane hydrochloride, 1-(3-hydroxyphenyl)-6-[3-(4-fluorobenzoyl)propyl]-6-azabicyclo[3,2,1]-octane hydrochloride, 1-(3-hydroxyphenyl)-6-phenethyl-7-methyl-6-azabicyclo[3,2,1]octane hydrochloride, (+)-1-(3-hydroxyphenyl)-6,7-dimethyl-6-azabicyclo[3,2,1]octane hydrobromide and (+)-1-(3-hydroxyphenyl)-6-methyl-6-azabicyclo[3,2,1]octane hydrochloride are 1.5, 0.27, 2.2, 2.0, 0.61, 1.2 and 3.7 mg/kg, respectively. In contrast thereto, the analgesic activity(=$ED_{50}$) of codein examined under the same condition as above is 9.5 mg/kg. The compound (I) of the present invention in which $R^3$ is alkanoyl, benzoyl or nicotinoyl are other examples of compounds having potent analgesic activity. For example, when examined under the same conditions as above, the analgesic activity (=$ED_{50}$) of 1-(3-acetyloxyphenyl)- and 1-(3-propionyloxyphenyl)-derivatives of 6,7-dimethyl-6-azabicyclo[3,2,1]octane are respectively 2.9 and 2.3 mg/kg.

Moreover, the toxicity of the compound (I) of the present invention is considerably low. For example, when administered subcutaneously to mice, the acute toxicity(=$LD_{50}$) of 1-(3-hydroxyphenyl)-6,7-dimethyl-6-azabicyclo[3,2,1]octane, its optically active (+)-isomer and 1-(3-propionyloxyphenyl)-6,7-dimethyl-6-azabicyclo[3,2,1]octane are about 113 to 123 mg/kg.

E. L. May et al. discloses that 5-(m-hydroxyphenyl)-2-methylmorphan and its optically active (-)-isomer show potent analgesic activity(e.f., Journal of Organic Chemistry 20(1955), 1197; Journal of Medicinal Chemistry 13(1970), 805). When a one % acetic acid solution is injected intraperitoneally to mice at the dose of 10 mg/kg after subcutaneous injection of a test compound and the number of writhings per mouse is counted for 5 minutes starting at 10 minutes after injection of acetic acid, the analgesic activity(= $ED_{50}$) of (−)-5-(m-hydroxyphenyl)-2-methylmorphan hydrochloride which would produce a 50% reduction in acetic acid-induced writhings is 3.0 mg/kg. As compared with said morphan compound, however, the compound (I) of the present invention is much more useful as an analgesic agent because of its reduced side effects such as less hypotensive activity and less decrease in heart rate. For example, (−)-5-(m-hydroxyphenyl)-2-methylmorphan hydrochloride, when administered intravenously to rabbits anesthetized with urethan(1.2 mg/kg, s.c), shows a decrease of 20 mmHg of the blood pressure at the dose of 0.048 mg/kg and a decrease of 20% of the heart rate at the dose of 0.21 mg/kg. Unlike said morphan compound, however, 1-(3-hydroxyphenyl)-6,7-dimethyl-6-azabicyclo[3,2,-1]octane hydrochloride and (+)-1-(3-hydroxyphenyl)-6,7-dimethyl-6-azabicyclo[3,2,1]octane hydrochloride of the present invention do not show a decrease of 20 mmHg of the blood pressure up to a dose of 10 mg/kg. Further, 1-(3-hydroxyphenyl)-6,7-dimethyl-6-azabicyclo[3,2,1]octane hydrochloride and (+)-1-(3-hydroxyphenyl)-6,7-dimethyl-6-azabicyclo[3,2,1]octane hydrochloride do not show a decrease of 20% of the heart rate up to a dose of 4.6 and 2.8 mg/kg, respectively. As seen from these facts, therefore, the compound (I) of the present invention has a greater safety as an analgesic agent in comparison with 5-(m-hydroxyphenyl)-2-methylmorphan.

The compound (I) of the present invention can be used for pharmaceutical use either in the form of a racemic modification or in an optically active form. It can also be used for pharmaceutical use either as the free base or a salt thereof. Pharmaceutically acceptable acid addition salts of the compound (I) include, for example, hydrochloride, hydrobromide, perchlorate, nitrate, sulfate, phosphate, formate, acetate, propionate, glycollate, lactate, pyruvate, oxalate, ascorbate, hydroxymaleate, phenylacetate, aminobenzoate, benzoate, methanesulfonate, malonate, succinate, maleate, fumarate, malate, citrate, tartrate, ethanesulfonate, phtalate, benzenesulfonate, p-toluenesulfonate, sulfanilate, aspartate and glutamate. The compound (I) of the invention may be used in the form of a pharmaceutical preparation for enteral or parenteral administration. The dose of the compound (I) suitable for pharmaceutical use may be 5 to 500 mg/body, especially 50 to 500 mg/body (for enteral administration) or 10 to 60 mg/body (for parenteral administration). Moreover, the compounds (I) of the present invention may be used in conjunction or admixture with a pharmaceutical excipient which is suitable for enteral or parenteral administration. The excipient selected should be the one that does not react with the compound (I) of the present invention. Suitable excipients include, for example, gelatin, lactose, glucose, sodium chloride, starch, magnesium stearate, talcum, vegetable oil, benzyl alcohol and gums. Other known medicinal excipients may be employed. The pharmaceutical preparation may be a solid dosage form such as a tablet, a coated tablet, a pill or a capsule, or a liquid dosage form such as a solution, a suspension of an emulsion. The pharmaceutical preparation may be sterilized and/or may contain auxiliaries such as preserving, stabilizing, wetting or emulsifying agents.

According to the present invention, the compound (I) can be prepared by the steps of

[A]

a. demethylating a 1-(3-methoxyphenyl)-6-azabicyclo[3,2,1]octane derivative of the formula:

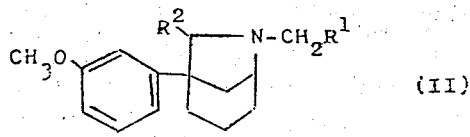

(II)

wherein $R^1$ and $R^2$ are the same as defined above, to give a 1-(3-hydroxyphenyl)-6-azabicyclo[3,2,1]octane derivative of the formula:

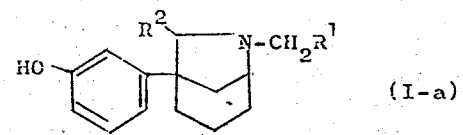

(I-a)

wherein $R^1$ and $R^2$ are the same as defined above, b. condensing a 1-(3-hydroxyphenyl)-6-azabicyclo[3,2,1]octane derivative of the formula:

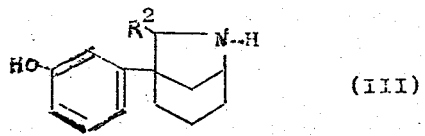

(III)

wherein $R^2$ is the same as defined above, with a compound of the formula:

$$R^1-CH_2X \quad (IV)$$

wherein X is halogen or a radical of the formula: $-N^+(CH_3)_3 \cdot I^-$, and $R^1$ is the same as defined above, to give the 1-(3-hydroxyphenyl)-6-azabicyclo[3,2,1]octane (I-a), or c. condensing the compound (III) with a carboxylic acid compound of the formula:

$$R^1-COOH \quad (V)$$

wherein $R^1$ is the same as defined above, or a functional derivative thereof, and then reducing the resultant N-acyl derivative of the compound (III) to give the 1-(3-hydroxyphenyl)-6-azabicyclo-[3,2,1]octane derivative(I-a), and, if required,

[B]

further acylating the compound (I-a) with a carboxylic acid compound of the formula:

$$R^4-OH \quad (VI)$$

wherein $R^4$ is alkanoyl of two to six carbon atoms, benzoyl or nicotinoyl, or a functional derivative thereof to give a 1-(3-acyloxyphenyl)-6-azabicyclo-[3,2,1]octane of the formula:

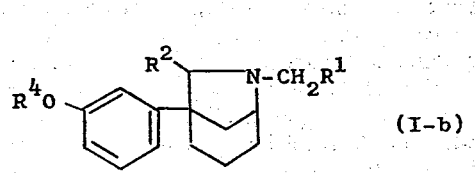

(I-b)

wherein $R^1$, $R^2$ and $R^4$ are the same as defined above.

Alternatively, the compound (I) of the present invention in which $R^1$ is hydrogen can be prepared by the steps of reductive methylation of the compound (III) to give a 1-(3-hydroxyphenyl)-6-methyl-6-azabicyclo[3,2,1]octane derivative of the formula:

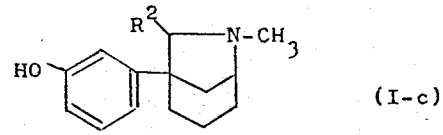

(I-c)

wherein $R^2$ is the same as defined above, and, if required, further acylating the compound (I-c) with the carboxylic acid compound (VI) or the functional derivative thereof.

In carrying out the above-mentioned reactions of the present invention, the starting compounds (II) and (III) can be employed either in the form of a racemic modification or in an optically active form. In addition, all of the above-mentioned reactions can be carried out without racemization. When the starting compounds (II) and (III) are employed in a racemic or optically active form during said reactions, therefore, the compound (I) of the present invention is obtained in the corresponding racemic or optically active form.

The demethylation reaction of the compound (II) can be accomplished by conventional manners. For example, the compound (I-a) of the invention is prepared by treating the compound (II) with hydrobromic acid, hydroiodic acid, aluminium chloride, boron chloride, boron bromide, pyridine hydrochloride and the like. Particularly, 47% hydrobromic acid is suitable for the purpose of the present invention. It is suitable to carry out the reaction at a temperature of $-20°$ to 200°C.

The condensation reaction of the compounds (III) and (IV) can be conducted in the presence of an acid acceptor. Organic and inorganic bases such as triethylamine, pyridine, quinoline, alkali metal acetate (e.g., potassium acetate, sodium acetate), alkali metal hydroxide (e.g., potassium hydroxide, sodium hydroxide) and alkali metal carbonate (e.g., potassium carbonate, sodium carbonate) are suitably employed as the acid acceptor. The condensation reaction may be carried out with or without a solvent. It is suitable to carry out the reaction at a temperature of 20° to 160°C. Preferred examples of the reaction solvent include acetone, toluene, dimethylformamide, dimethylsulfoxide and a lower alkanol (e.g., methanol, ethanol, propanol).

The condensation reaction of the compound (III) with the carboxylic acid compound (V) or the functional derivative thereof can be accomplished by conventional manners. For example, when the functional derivative of the compound (V) is employed for the reaction, the condensation reaction is preferably carried out in the carbonate) are of an acid acceptor. Examples of the functional derivative of the compound (V) which are suitable for use in the present invention include the corresponding acid anhydride, acid halide (e.g., chloride, bromide) and acid esters(e.g., methyl ester, ethyl ester, propyl ester, benzyl ester). Organic and inorganic bases such as triethylamine, pyridine, quinoline, alkali metal acetate(e.g., potassium acetate, sodium acetate), alkali metal hydroxide(e.g., potassium hydroxide, sodium hydroxide) and alkali metal carbonate(e.g., potassium carbonate, sodium carbonate)are examples of suitable acid acceptors. The reaction can be carried out with or without a solvent. It is suitable to carry out the reaction at a temperature of 0° to 120°C. Preferred examples of the reaction solvent include dichloromethane and dimethylformamide. Alternatively, when the compound (V) in the form of free acid is employed, the N-acyl derivative of the compound (III) is prepared by reacting the compound (III) with an approximately equal amount of the compound (V) in the presence of a dehydrating agent at a temperature of −10° to 80°C. N,N′-dicyclohexylcarbodiimide, N-cyclohexyl-N′-morpholinomethylcarbodiimide and the like are employed as the dehydrating agent. Tetrahydrofuran and dimethylformamide are suitable as the reaction solvent. The resultant N-acyl derivative of the compound (III) can be readily converted to the compound (I-a) by reacting said N-acyl derivative with a conventional reducing agent in a solvent. Suitable examples of the reducing agent include lithium aluminium hydride, aluminium hydride and diborane. It is preferred to carry out the reduction at a temperature of 25° to 70°C. Tetrahydrofuran and ether are suitable as the reaction solvent.

Moreover, the reductive methylation of the compound (III) can be accomplished by condensing the compound (III) with formaldehyde or alkyl chloroformate(e.g., methyl chloroformate, ethyl chloroformate, propyl chloroformate) in a solvent, followed by reduction or catalytic hydrogenation of the resultant condensation product. The condensation reaction of the compound (III) with formaldehyde or alkyl chloroformate is preferably carried out at a temperature of 0° to 100°C. A lower alkanol(e.g., methanol, ethanol, propanol), chloroform and dimethylformamide are suitable as the reaction solvent. The subsequent reduction of the condensation product is carried out by treatment with alkali metal borohydride or lithium aluminium hydride in a solvent. Sodium borohydride, potassium borohydride and lithium borohydride are employed as the alkali metal borohydride. Preferred examples of the reaction solvent include tetrahydrofuran, ether, dioxane and a lower alkanol(e.g., methanol, ethanol, propanol). It is preferred to carry out the reduction at a temperature of 20° to 80°C. On the other hand, the catalytic hydrogenation of the condensation product is conducted in the presence of a catalyst in a hydrogen atmosphere in a solvent. Preferred examples of the catalyst include platinum dioxide, platinum, palladium-carbon and Raney-nickel. A lower alkanol such as methanol, ethanol or propanol is suitable as the reaction solvent. Said catalytic hydrogenation is preferably carried out at a temperature of 20° to 40°C.

The compounds (I-a) and (I-c) of the present invention which can be obtained in the above-mentioned procedures may be, if required, further acylated with the carboxylic acid compound (VI) or a functional derivative thereof. Said acylation reaction is readily carried out. For example, when the functional derivative of the compound (VI) is employed, the acylation reaction is carried out in the presence of an acid acceptor. Suitable examples of the functional derivative of the compound (VI) include the corresponding acid anhydride and acid halide(e.g., chloride, bromide). Organic and inorganic bases such as triethylamine, pyridine, quinoline, alkali metal acetate(e.g., potassium acetate, sodium acetate), alkali metal hydroxide (e.g., potassium hydroxide, sodium hydroxide) and alkali metal carbonate(e.g., potassium carbonate, sodium carbonate) are exemplified as the acid acceptor. The reaction may be carried out with or without a solvent. It is suitable to carry out the acylation at a temperature of 0° to 180°C. Preferred examples of the reaction solvent include benzene, toluene and dichloromethane. Alternatively, when the compound (VI) in the form of free acid is employed, the acylation reaction is carried out by treatment of the compound (I-a or c) with an approximately equal amount of the compound (VI) in the presence of a dehydrating agent at a temperature of −10° to 80°C. N,N′-dicyclohexylcarbodiimide, N-cyclohexyl-N′-morpholinomethylcarbodiimide and the like are employed as the dehydrating agent. Tetrahydrofuran and dimethylformamide are suitable as the reaction solvent.

All of the starting compounds (II) and (III) of the present invention which are employed in the steps of [A]-a) through [B] and in the step of the reductive methylation are novel compounds. These novel starting compounds can be prepared in accordance with several methods illustrated by the following reaction scheme:

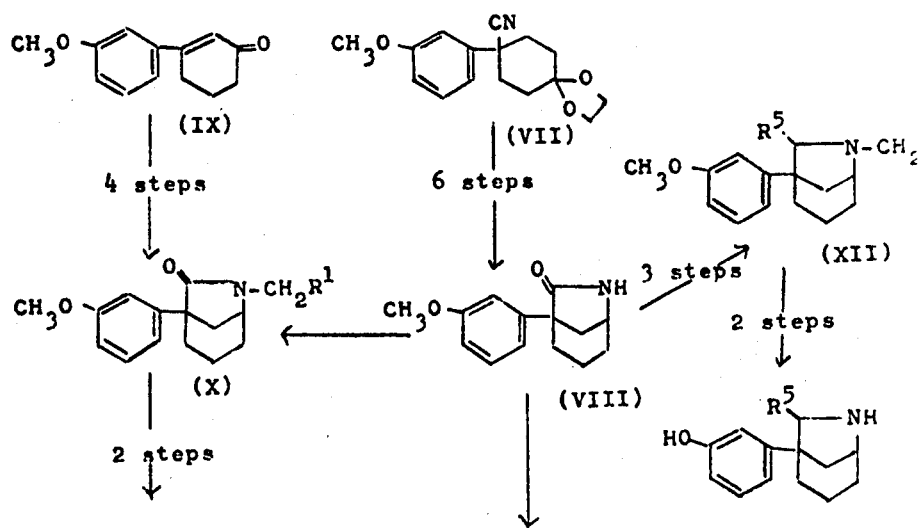

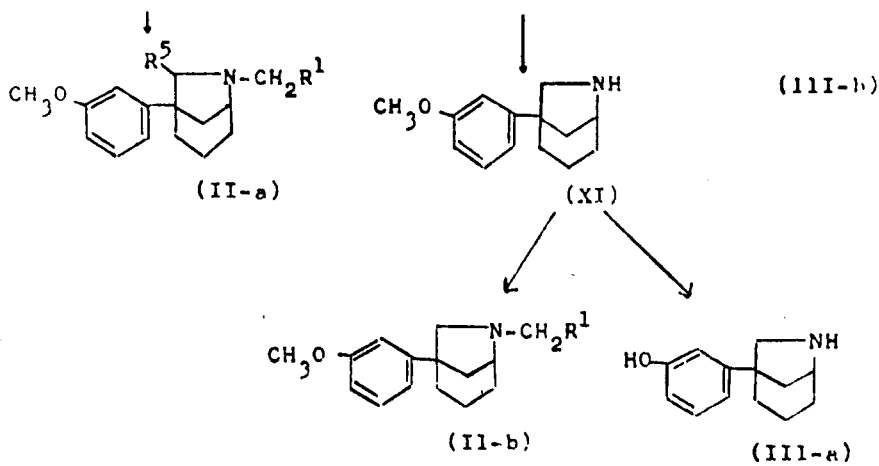

wherein $R^5$ is alkyl of one to three carbon atoms, and $R^1$ is the same as defined above.

The following are the explanations of each of the reactions illustrated above:

First of all, 1-(3-methoxyphenyl)-6-azabicyclo[3,2,1]-octane-7-one (VIII) is prepared by the six steps of (1) hydrolyzing 4-(3-methoxyphenyl)-4-cyano-1,1,-ethylenedioxy-cyclohexane (VII) with an alkali metal hydroxide(e.g., sodium hydroxide, potassium hydroxide) under heating in a solvent (e.g., methanol, ethanol, ethyleneglycol, a mixture of one of these solvents and water) to give 4-(3-methoxyphenyl)-4-carbamoyl-1,1-ethylenedioxy-cyclohexane, (2) reacting said carbamoyl-cyclohexane with an acid(e.g., hydrochloric acid, sulfuric acid, acetic acid) under heating, (3) brominating the resultant 4-(3-methoxyphenyl)-4-carbamoyl-cyclohexanone with bromine or pyridinium hydrobromide perbromide ($C_5H_5N^+HBr^-$) at room temperature in a solvent (e.g., acetic acid, tetrahydrofuran), (4) reacting the resultant 2-bromo-4-(3-methoxyphenyl)-4-carbamoyl-cyclohexanone with an alkali metal hydride (e.g., sodium hydride) or an alkali metal alkoxide (e.g., sodium methoxide, potassium methoxide, sodium ethoxide, potassium ethoxide) at room temperature in a solvent(e.g., methanol, ethanol, dimethoxyethane) to give 1-(3-methoxyphenyl)-6-azabicyclo[3,2,1]octane-4,7-dione, (5) refluxing a mixture of said product and hydrazine hydrate under heating in a solvent (e.g., ethanol, ethyleneglycol), and then (6) heating the resultant 1-(3-methoxyphenyl)-6-azabicyclo[3,2,1]octane-4,7-dione-4-hydrazone in the presence of an alkali agent(e.g., potassium hydroxide, potassium tert.-butoxide) in a solvent (e.g., toluene).

A 1-(3-methoxyphenyl)-6-azabicyclo[3,2,1]octane-7-one derivative (X) is prepared by condensing the compound (VIII) or an alkali metal salt(e.g., sodium salt, potassium salt) thereof with the compound (IV). This condensation reaction is carried out in the same manner as used in the condensation reaction of the compounds (III) and (IV). Alternatively, the 1-(3-methoxyphenyl)-6-azabicyclo[3,2,1]octane derivative (X) is prepared by the four steps of (1) reacting 1-(3-methoxyphenyl)-cyclohexene-3-one (IX) with an alkali metal cyanide (e.g., potassium cyanide, sodium cyanide) in the presence of acetic acid, ammonium chloride or triethylamine hydrochloride under heating in a solvent (e.g., methanol, ethanol, propanol, dimethylformamide), (2) refluxing a mixture of the resultant 3-(3-methoxyphenyl)-3-cyano-cyclohexanone and an alkanol (e.g., methanol, ethanol) under an acidic condition to give an alkyl 1-(3-methoxyphenyl)-3-oxo-cyclohexane-1-carboxylate, (3) subjecting a mixture of said carboxylate and alkylamine(e.g., methylamine, ethylamine, propylamine, butylamine) to catalytic hydrogenation at room temperature in the presence of a catalyst(e.g., platinum, platinum dioxide, Raney-nickel, palladium-carbon) in a solvent(e.g., methanol, ethanol, propanol), and then (4) heating the resultant alkyl 1-(3-methoxyphenyl)-3-alkylamino-cyclohexane-1-carboxylate in a solvent (e.g., toluene, xylene).

The compound (II-a) is prepared by the steps of refluxing a mixture of the compound (X) and an alkyl lithium or alkyl magnesium halide in a solvent(e.g., ether, benzene, tetrahydrofuran) to give a 7-alkylidene derivative of the compound (X), and reducing said alkylidene derivative with an alkali metal borohydride (e.g., sodium borohydride) at room temperature in a solvent (e.g., methanol, ethanol).

Reduction of the compound (VIII) with either one of lithium aluminium hydride, aluminium hydride and diborane yields 1-(3-methoxyphenyl)-6-azabicyclo[3,2,1]octane (XI). Said reduction is carried out in the same manner as used in reducing the N-acyl derivative of the compound (III).

The compounds (II-a) and (XI) mentioned in the above procedures are always obtained in the form of a racemic modification and may be, if required, resolved into each of the optically active enantiomers. The resolution of the compound (II) or (XI) into each of its optically active enantiomers may be conducted by reacting the racemic modification of the compound (II) or (XI) with a resolving agent in a solvent to form the diastereoisomeric salt thereof, and separating the diastereoisomers into each components by selective crystallization. Suitable examples of the resolving agent include d-tartaric acid or its derivatives (e.g., dibenzoyl-d-tartaric acid, monobenzoyl-d-tartaric acid, diacetyl-d-tartaric acid), d-camphorsulfonic acid, d-α-bromocamphorsulfonic acid, l-mandelic acid, quinic acid, glutamic acid or its derivative(e.g., N-carbobenzyloxyglutamic acid). Water, a lower alkanol(e.g., methanol, ethanol, propanol, butanol), ethylacetate, dimethylformamide, or a mixture of water and one of the lower alkanols or dimethylformamide are suitable as the solvent. The selective crystallization may be preferably carried out at room temperature.

The compound (XI) is readily converted to a 1-(3-methoxyphenyl)-6-azabicyclo[3,2,1]octane derivative (II-b) in the same manner as used in converting the compound (III) into the compound (I-a) or (I-c). On the other hand, demethylation of the compound (XI) affords 1-(3-hydroxyphenyl)-6-azabicylco[3,2,1]octane (III-a). Said demethylation is carried out in the same manner as used in demethylating the compound (II).

1-(3-methoxyphenyl)-6-benzyl-7-alkyl-6-azabicyclo[3,2,1]octane (XII) is prepared by the three steps of (1) condensing the compound (VIII) or an alkali metal salt(e.g., sodium salt, potassium salt) thereof with benzyl halide under heating in a solvent(e.g., dioxane), (2) refluxing a mixture of the resultant 1-(3-methoxyphenyl)-6-benzyl-7-oxo-6-azabicyclo[3,2,1]octane and an alkyllithium or alkyl magnesium halide in a solvent-(e.g., ether, benzene, tetrahydrofuran) to give 1-(3-methoxyphenyl)-6-benzyl-7-alkylidene-6-azabicyclo[3,2,1]octane, and then (3) reducing said alkylidene derivative with an alkali metal borohydride(e.g., sodium borohydride) at room temperature in a solvent.

Further, 1-(3-hydroxyphenyl)-7-alkyl-6-azabicyclo[3,2,1]octane (III-b) is prepared by catalytic hydrogenation of the compound (XII), followed by demethylation thereof. The catalytic hydrogenation is carried out at room temperature in the presence of a catalyst-(e.g., platinum, platinum dioxide, palladium) in a solvent(e.g., methanol, ethanol, acetic acid). The subsequent demethylation is carried out in the same manner as used in demethylating the compound (II).

Practical and presently-preferred embodiments of the present invention are illustratively shown in the following Examples.

EXAMPLE 1

1-(3-methoxyphenyl)-6-azabicyclo[3,2,1]octane-7-one a. A mixture of 3.5 g of 4-(3-methoxyphenyl)-4-cyano-1,1-ethylenedioxy-cyclohexane, 70 ml of 5% aqueous potassium hydroxide and 70 ml of ethanol is refluxed for 22 hours. After cooling, the mixture is diluted with water, and then extracted with chloroform. The chloroform extract is dried and evaporated to remove solvent. The residue thus obtained is recrystallized from a mixture of ethylacetate and n-hexane. 2.32 g of 4-(3-methoxyphenyl)-4-carbamoyl-1,1-ethylenedioxy-cyclohexane are obtained. M.p. 135° – 138°C.

b. A mixture of 8.7 g of 4-(3-methoxyphenyl)-4-carbamoyl-1,1,-ethylenedioxy-cyclohexane and 170 ml of acetic acid is refluxed for 15 hours. After the reaction, the mixture is evaporated under reduced pressure to remove acetic acid. The residue is dissolved in benzene. The benzene solution is washed with aqueous sodium bicarbonate, dried aand then evaporated to remove benzene. The residue thus obtained is recrystallized from ethylacetate. 5.4 g of 4-(3-methoxyphenyl)-4-carbamoyl-cyclohexane are obtained. M.p. 120°–122°C.

c. 50.5 g of 4-(3-methoxyphenyl)-4-carbamoyl-cyclohexanone are dissolved in 500 ml of acetic acid, and a solution of 32.7 g of bromine in 500 ml of acetic acid is added dropwise thereto at 20°C. under stirring. Then, the mixture is poured into ice-water and extracted with chloroform. The chloroform extract is washed with water, dried and then evaporated to remove solvent. 69.8 g of 2-bromo-4-(3-methoxyphenyl)-4-carbamoyl-cyclohexanone are obtained as crude oil.

d. 69.8 g of 2-bromo-4-(3-methoxyphenyl)-4-carbamoyl-cyclohexanone obtained above are dissolved in 250 ml of methanol. A sodium methoxide solution prepared from 18.8 g of sodium and 500 ml of methanol is added thereto. The mixture is stirred at room temperature for 1 hour and then concentrated under reduced pressure. 1000 ml of water are added to the residue, and the aqueous mixture is extracted with chloroform. The chloroform extract is washed with an aqueous solution saturated with sodium chloride. Then, the chloroform extract is dried and evaporated to remove solvent. The residue thus obtained is recrystallized from ethylacetate. 25.2 g of 1-(3-methoxyphenyl)-6-azabicyclo[3,2,1]octane-4,7-dione are obtained. M.p. 138° – 139°C.

e. A mixture of 21.73 g of 1-(3-methoxyphenyl)-6-azabicyclo[3,2,1]octane-4,7-dione, 4.9 g of hydrazine hydrate and 170 ml of ethanol is refluxed for 1 hour. After cooling, the mixture is evaporated under reduced pressure to remove solvent. The residue thus obtained is dispersed in benzene and then filtered to give 21.64 g of 1-(3-methoxyphenyl)-6-azabicyclo[3,2,1]octane-4,7-dione-4-hydrazone as crude crystals. A mixture of 21.64 g of 1-(3-methoxyphenyl)-6-azabicyclo[3,2,1]octane-4,7-dione-4-hydrazone, 17.1 g of potassium tert.-butoxide and 400 ml of toluene is refluxed for 2 hours under heating. After cooling, water is added to the mixture, and the aqueous mixture is extracted with ether. The ether extract is washed with water, dried and then evaporated to remove solvent. The residue thus obtained is recrystallized from a mixture of ethylacetate and n-hexane. 17.54 g of 1-(3-methoxyphenyl)-6-azabicyclo[3,2,1]octane-7-one are obtained. M.p. 109° – 111°C.

EXAMPLE 2

1-(3-methoxyphenyl)-6-methyl-6-azabicyclo[3,2,1]octane-7-one 0.36 g of 69% sodium hydride is added to 40 ml of dimethylsulfoxide, The mixture is heated at 70°C for 30 minutes in a nitrogen atmosphere. 2 g of 1-(3-methoxyphenyl)-6-azabicyclo[3,2,1]octane-7-one are added to the mixture at 10° to 15°C. Then, the mixture is stirred at room temperature for 1 hour. 2.1 G of methyl iodide are added to the mixture, and the mixture is further stirred at room temperature for 2 hours. The reaction mixture is poured into ice-water and extracted with ether. The ether extract is washed with water, dried and then evaporated to remove solvent. The residue thus obtained is recrystallized from n-hexane. 2 g of 1-(3-methoxyphenyl)-6-methyl-6-azabicyclo[3,2,1]octane-7-one are obtained. M.p. 68° – 70°C.

EXAMPLE 3

1-(3-methoxyphenyl)-6-methyl-6-azabicyclo[3,2,1]octane-7-one a. A solution of 8.0 g of potassium cyanide in 28 ml of water is added under stirring to a mixture of 4.04 g of 1-(3-methoxyphenyl)-cyclohexene-3-one, 120 ml of 95% ethanol and 3.6 g of acetic acid. The mixture is stirred at 35°C for 80 hours. After the reaction, 260 ml of water are added to the mixture, and the aqueous mixture is extracted with chloroform. The chloroform extract is washed with water, dried and then evaporated to remove solvent. The residue thus obtained is distilled under reduced pressure, whereby 3 g of 3-(3-methoxyphenyl)-3-cyano-cyclohexanone are obtained as an oil boiling at 175°C/o.8 mmHg. M.p. 48° – 48.5°C(recrystallized from isopropyl ether).

b. A mixture of 4 g of 3-(3-methoxyphenyl)-3-cyano-cyclohexanone and 45 ml of a 36% hydrogen chloride-ethanol solution is refluxed for 4 hours under heating. After the reaction, the mixture is concentrated under reduced pressure. Water is added to the residue, and the aqueous mixture is extracted with ether. The ether extract is washed with water, dried and then evaporated to remove solvent. The residue is distilled under reduced pressure, whereby 4.1 g of methyl 1-(3-methoxyphenyl)-3-oxo-cyclohexane-1-carboxylate are obtained as an oil boiling at 176°C/2–3 mmHg.

c. A mixture of 0.52 g of methyl 1-(3-methoxyphenyl)-3-oxo-cyclohexane-1-carboxylate, 0.5 ml of 30% aqueous methylamine, 8 ml of methanol and 0.025 g of platinum oxide is shaken for 48 hours in a hydrogen atmosphere. After the reaction, the mixture is filtered to remove the catalyst. The filtrate is concentrated under reduced pressure to remove solvent, whereby methyl 1-(3-methoxyphenyl)-3-methylamino-cyclohexane-1-carboxylate is obtained as crude oil. 7 ml of xylene are added to the crude oil and the mixture is refluxed for 20 hours under heating. Then, the mixture is concentrated under reduced pressure to remove solvent. The residue is dissolved in ether. The ether solution is washed with 10% hydrochloric acid and water, successively, dried and then evaporated to remove solvent. The residue thus obtained is recrystallized from n-hexane. 0.33 g of 1-(14 3-methoxyphenyl)-6-methyl-6-azabicyclo[3,2,1]octane-7-one is obtained. M.p. 68° – 70°C.

EXAMPLE 4

1-(3-methoxyphenyl)-6-methyl-6-azabicyclo[3,2,1]octane-7-one a. A mixture of 6.06 g of 1-(3-methoxyphenyl)-cyclohexene-3-one, 4.02 g of potassium cyanide, 4.33 g of trimethylamine hydrochloride, 21 ml of water and 120 ml of dimethylformamide is stirred at 93° to 94°C for 6 hours. After the reaction, the mixture is concentrated under reduced pressure. Benzene is added to the residue, and the insoluble materials are filtered off. The filtrate is washed with water, 10% hydrochloric acid and water, successively. Then, the filtrate is dried and evaporated to remove solvent. The residue thus obtained is distilled under reduced pressure, whereby 5.26 g of 3-(3-methoxyphenyl)-3-cyano-cyclohexanone are obtained as an oil boiling at 175°C/0.8 mmHg. M.p. 48° – 48.5°C(crystallized with isopropylether).

b. A solution of 9.5 g of 3-(3-methoxyphenyl)-3-cyano-cyclohexanone in 95 ml of methanol is saturated with gaseous hydrogen chloride under ice-cooling. The solution is refluxed for 4 hours under heating. Then, the solution is concentrated under reduced pressure. Water is added to the residue, and the aqueous mixture is extracted with benzene. The benzene extract is washed with water, aqueous sodium bicarbonate and water, successively, dried and then evaporated to remove solvent. The residue thus obtained is distilled under reduced pressure, whereby 9.55 g of methyl 1-(3-methoxyphenyl)-3-oxo-cyclohexane-1-carboxylate are obtained as a colorless oil boiling at 176°C/2–3 mmHg.

c. A mixture of 9.29 g of methyl 1-(3-methoxyphenyl)-3-oxo-cyclohexane-1-carboxylate, 5.5 ml of 40% aqueous methylamine and 0.13 g of platinum oxide is shaken at room temperature for 5 hours in a hydrogen atmosphere under atmospheric pressure. The mixture absorbs about 790 ml of hydrogen. After the reaction, the mixture is filtered to remove the catalyst. The filtrate is concentrated under reduced pressure. The residue thus obtained is heated at 100° to 110°C for 2 hours under reduced pressure, and then dissolved in benzene. The benzene solution is washed with 10% hydrochloric acid and water, successively. Then, the benzene solution is evaporated to remove solvent. The residue thus obtained is recrystallized from isopropylether. 5.8 g of 1-(3-methoxyphenyl)-6-methyl-6azabicyclo[3,2,1]octane-7-one are obtained. M.p. 68° – 70°C.

EXAMPLE 5

1-(3-methoxyphenyl)-6,7-dimethyl-6-azabicyclo[3,2,1]octane 0.17 g of lithium is added to 8 ml of absolute ether in a nitrogen atmosphere, and a solution of 1.6 g of methyl iodide in 3 ml of absolute ether is added dropwise thereto at 0° to −5°C. The mixture is stirred at the same temperature for 30 minutes. Then, a solution of 1.0 g of 1-(3-methoxyphenyl)-6-methyl-6-azabicyclo[3,2,1]octane-7-one in 30 ml of benzene is added dropwise to the mixture at room temperature for 5 minutes. The mixture is refluxed for 3 hours. Water is added to the mixture under ice-cooling, and the aqueous mixture is extracted with ether. The ether extract is washed with water, dried and then evaporated to remove solvent, whereby 1.0 g of 1-(3-methoxyphenyl)-6-methyl-7-methylidene-6-azabicyclo[3,2,1]octane is obtained. The product thus obtained is dissolved in 60 ml of ethanol. 300 mg of sodium borohydride are added to the ethanol solution at 10° to 15°C. Then, the mixture is stirred at room temperature for 20 hours. After the reaction, the mixture is concentrated under reduced pressure. Water is added to the residue, and the aqueous mixture is extracted with chloroform. The chloroform extract is washed with water, dried and then evaporated to remove solvent. Methanolic hydrogen bromide is added to the residue in ether, and the crystalline precipitate is collected by filtration. The precipitate is recrystallized from a mixture of ethanol, acetone and ether. 1.1 g of 1-(3-methoxyphenyl)-6,7-dimethyl-6-azabicyclo[3,2,1]octane hydrobromide are obtained. M.p. 175° – 177°C.

EXAMPLE 6

1-(3-methoxyphenyl)-6-methyl-7-ethyl-6-azabicyclo[3,2,1]octane 0.17 g of lithium is added to 8 ml of absolute ether in a nitrogen atmosphere, and a solution of 1.8 g of ethyl iodide in 3 ml of absolute ether is added dropwise thereto at 0° to −5°C. The mixture is stirred at the same temperature for 30 minutes. Then, a solution of 0.8 g of 1-(3-methoxyphenyl)-6-methyl-6-azabicyclo[3,2,1]octane-7-one in 30 ml of benzene is added dropwise to the mixture at room temperature for 5 minutes. The mixture is refluxed for 3 hours. Water is added to the mixture under ice-cooling, and the aqueous mixture thus obtained is extracted with ether. The ether extract is washed with water, dried and then evaporated to remove solvent, whereby 0.8 g of 1-(3-methoxyphenyl)-6-methyl-7-ethylidene-6-azabicyclo[3,2,1]octane is obtained. The product thus obtained is dissolved in 60 ml of ethanol. 300 mg of sodium borohydride are added to the ethanol solution at 10° to 15°C. Then, the mixture is stirred at room temperature for 20 hours. After the reaction, the mixture is concentrated under reduced pressure. Water is added to the residue, and the aqueous mixture is extracted with chloroform. The chloroform extract is washed with water, dried and then evaporated to remove solvent. Methanolic hydrogen chloride is added to the residue in ether, and the crystalline precipitate is collected by filtration. The precipitate is recrystallized from a mixture of ethanol and ether. 0.4 g of 1-(3-methoxyphenyl)-6-methyl-7-ethyl-6-azabicyclo[3,2,1]octane hydrochloride is obtained. M.p. 176°– 178°C.

EXAMPLE 7

Optically active 1-(3-methoxyphenyl)-6,7-dimethyl-6-azabicyclo[3,2,1]octane 8.5 g of 1-(3-methoxyphenyl)-6,7-dimethyl-6-azabicyclo[3,2,1]octane and 5.3 g of d-tartaric acid are dissolved in 50 ml of ethanol under heating. The solution is concentrated to dryness under reduced pressure. Then, the residue is recrystallized twice from 25 ml of methanol. 6.01 g of (−)-1-(3-methoxyphenyl)-6,7-dimethyl-6-azabicyclo[3,2,1]octane d-tartarate are obtained as crystals. M.p. 174° – 176°C. $[\alpha]_D^{23}$ + 22.3°(c = 1.6, methanol)

Free base: $[\alpha]_D^{23}$ − 10.4°(c = 0.76, methanol)

The methanol filtrate which is obtained after isolation of (−)-1-(3-methoxyphenyl)-6,7-dimethyl-6-azabicyclo[3,2,1]octane d-tartarate is concentrated to dryness. The residue thus obtained is recrystallized from 15 ml of methanol. 5.45 g of (+)-1-(3-methoxyphenyl)-6,7-dimethyl-6-azabicyclo[3,2,1]octane d-tartarate are obtained. M.p. 143 – 146°C. $[\alpha]_D^{23}$ + 0.5°(c = 1.205, methanol)

Free base: $[\alpha]_D^{23}$ + 10.3°(c = 0.75, methanol)

EXAMPLE 8

1-(3-methoxyphenyl)-6-azabicyclo[3,2,1]octane

A mixture of 3 g of 1-(3-methoxyphenyl)-6-azabicyclo[3,2,1]octane-7-one, 2.7 g of lithium aluminium hydride and 150 ml of tetrahydrofuran is refluxed for 5 hours under heating. After cooling, 6 ml of water are added to the mixture to decompose lithium aluminium hydride. Then, 100 ml of ether are added to the aqueous mixture, and the aqueous mixture is filtered to remove insoluble materials. The filtrate is dried and then evaporated to remove solvent. Methanolic oxalic acid solution is added to the residue in ether, and the crystalline precipitate is collected by filtration. The precipitate is recrystallized from ethanol. 3.65 g of 1-(3-methoxyphenyl)-6-azabicyclo[3,2,1]octane oxalate are obtained. M.p. 173° – 175°C.

EXAMPLE 9

Optically active 1-(3-methoxyphenyl)-6-azabicyclo[3,2,1]octane 8.7 g of 1-(3-methoxyphenyl)-6-azabicyclo[3,2,1]octane and 6.2 g of d-tartaric acid are added to 80 ml of boiling-ethanol. The mixture is allowed to stand overnight. The crystalline precipitate is collected by filtration and then recrystallized from methanol. 5.65 g of (−)-1-(3-methoxyphenyl)-6-azabicyclo[3,2,1]octane d-tartarate are obtained. M.p. 190° – 192°C.

Free base: $[\alpha]_D^{23}$ − 15.3°(c = 0.64, methanol)

The methanol filtrate which is obtained after isolation of (−)-1-(3-methoxyphenyl)-6-azabicyclo[3,2,1]octane d-tartarate is concentrated under reduced pressure. Aqueous ammonia is added to the residue, and the resultant mixture is extracted with ether. The ether extract is washed with water, dried and then evaporated to remove solvent. The residue thus obtained is dissolved in 30 ml of ethanol, and 4 g of l-malic acid are added to the solution. The solution is allowed to stand overnight. The crystalline precipitate is collected by filtration and then recrystallized from ethanol. 5.2 g of (+)-1-(3-methoxyphenyl)-6-azabicyclo[3,2,1]octane l-malate are obtained. M.p. 132° – 133°C. Free base: $[\alpha]_D^{23}$ + 15.3°(c = 0.69, methanol)

EXAMPLE 10

1-(3-methoxyphenyl)-6-methyl-6-azabicyclo[3,2,1]octane 0.85 g of 1-(3-methoxyphenyl)-6-azabicyclo[3,2,1]octane is dissolved in 10 ml of ethanol, and 0.34 g of 37% formalin is added thereto. The solution is heated for 30 minutes on a water bath. After cooling, 0.54 g of sodium borohydride is added to the solution. The solution is stirred at room temperature for 2 hours and then concentrated under reduced pressure to remove solvent. Water is added to the residue, and the aqueous mixture is extracted with chloroform. The chloroform extract is washed with water, dried and then evaporated to remove solvent. Methanolic hydrogen bromide is added to the residue in ether, and the crystalline precipitate is collected by filtration. The precipitate is recrystallized from a mixture of ethanol and ether. 0.81 g of 1-(3-methoxyphenyl)-6-methyl-6-azabicyclo[3,2,1]octane hydrobromide is obtained. M.p. 169° – 171°C.

The following compounds are prepared in the same manner as described above:

(+)-1-(3-methoxyphenyl)-6-methyl-6-azabicyclo[3,2,1]octane picrate: M.p. 140° – 142°C. $[\alpha]_D^{23}$ + 67.5°(c = 0.4, chloroform)

(−)-1-(3-methoxyphenyl)-6-methyl-6-azabicyclo[3,2,1]octane picrate: M.p. 140° – 142°C. $[\alpha]_D^{23}$ − 68.2°(c = 0.39, chloroform)

EXAMPLE 11

1-(3-methoxyphenyl)-6-(3-benzoylpropyl)-6-azabicyclo[3,2,1]octane

A mixture of 0.8 g of 1-(3-methoxyphenyl)-6-azabicyclo[3,2,1]octane, 0.74 g of 3-benzoylpropyl chloride, 0.8 g of potassium carbonate, 0.05 g of potassium iodide and 20 ml of toluene is refluxed for 24 hours. After cooling, water is added to the mixture, and the aqueous mixture is extracted with ether. The ether extract is washed with water, dried and then evaporated to remove solvent. The residue thus obtained is dissolved in 2 ml of benzene. The benzene solution is poured onto a column of 50 g of aluminium oxide. Then, the column is eluted with a mixture of 400 ml of benzene and 400 ml of n-hexane, and the effluent is evaporated to remove solvent. Methanolic hydrogen chloride is added to the residue in ether, and the crystalline precipitate is collected by filtration. The precipitate is recrystallized from a mixture of ethanol and ether. 0.485 g of 1-(3-methoxyphenyl)- 6-(3-benzoylpropyl)-6-azabicyclo[3,2,1]octane hydrochloride is obtained. M.p. 167° – 169°C.

EXAMPLE 12

1-(3-methoxyphenyl)-6-[3-(4-fluorobenzoyl)propyl]-6-azabicyclo[3,2,1]octane

A mixture of 0.8 g of 1-(3-methoxyphenyl)-6-azabicyclo[3,2,1]octane, 0.81 g of 3-(4-fluorobenzoyl)propyl chloride, 0.8 g of potassium carbonate, 0.03 g of potassium iodide and 20 ml of toluene is refluxed for 48 hours. After cooling, the mixture is treated in the same manner as described in Example 11. 0.65 g of 1-(3-methoxyphenyl)-6-[3-(4-fluorobenzoyl)propyl]-6-azabicyclo[3,2,1]octane hydrochloride is obtained. M.p. 195° – 196°C(recrystallized from a mixture of ethanol and ether).

EXAMPLE 13

1-(3-hydroxyphenyl)-6-azabicyclo[3,2,1]octane

A mixture of 9 g of 1-(3-methoxyphenyl)-6-azabicyclo[3,2,1]octane oxalate and 90 ml of aqueous 48% hydrobromic acid is refluxed for 1.5 hours. After the reaction, the mixture is concentrated under reduced pressure. The residue thus obtained is recrystallized from a mixture of ethanol and ether. 7.7 g of 1-(3-hydroxyphenyl)-6-azabicyclo[3,2,1]octane hydrobromide are obtained. M.p. 239° – 242°C.

EXAMPLE 14

1-(3-methoxyphenyl)-6-benzyl-7-methyl-6-azabicyclo[3,2,1]octane a. A mixture of 2.31 g of 1-(3-methoxyphenyl)-6-azabicyclo[3,2,1]octane-7-one, 0.418 g of 69% sodium hydride and 30 ml of dioxane is stirred at 60° to 62°C for one hour. After cooling, 1.52 g of benzyl chloride are added to the solution. Then, the solution is further stirred at 100°C for 3 hours. After cooling, water is added to the solution. The solution is evaporated to remove solvent. Then, water is added to the residue, and the aqueous mixture is extracted with ether. The ether extract is dried and then evaporated to remove solvent. The residue thus obtained is distilled under reduced pressure, whereby 3.17 g of 1-(3-methoxyphenyl)-6-benzyl-6-azabicyclo[3,2,1]octane-7-one are obtained as a viscous oil boiling at 195°C(bath temperature)/0.05 mmHg.

b. 0.262 g of lithium is added to 10 ml of absolute ether in a nitrogen atmosphere, and a solution of 2.8 g of methyl iodide in 5 ml of absolute ether is added dropwise thereto at 0° to 5°C. The mixture is stirred at the same temperature for 50 minutes. Then, a solution of 1.5 g of 1-(3-methoxyphenyl)-6-benzyl-6-azabicyclo[3,2,1]octane-7-one in 30 ml of absolute benzene is added dropwise to the mixture at 5° to 10°C in a nitrogen atmosphere. The mixture is stirred at room temperature overnight. After water is added to the mixture, the benzene-ether layer is washed with water, dried and then evaporated to remove solvent. The residue thus obtained is dissolved in 60 ml of ethanol, and 0.355 g of sodium borohydride is added to the ethanol solution at 8° to 10°C. The ethanol solution is stirred at room temperature for 2 hours. Then, the ethanol solution is concentrated under reduced pressure to remove solvent. water is added to the residue, and the aqueous mixture is extracted with ether. The ether extract is extracted with 10% aqueous hydrochloric acid. The aqueous extract is washed with ether, made alkaline with ammonia and again extracted with ether. The ether extract thus obtained is dried and evaporated to remove solvent. The residue is dissolved in 5 ml of chloroform. The chloroform solution is poured onto a column of 100 g of silica gel. Then, the column is eluted with a mixture of 2850 ml of chloroform and 150 ml of methanol. The effluent obtained is evaporated to remove solvent, whereby 0.59 g of 1-(3-methoxyphenyl)-6-benzyl-7-methyl-6-azabicyclo[3,2,-1]octane is obtained. Picrate: M.p. 184°–186°C(recrystallized from methanol).

EXAMPLE 15

1-(3-hydroxyphenyl)-7-methyl-6-azabicyclo[3,2,1]octane (a) A mixture of 7.21 g of 1-(3-methoxyphenyl)-6-benzyl-7-methyl-6-azabicyclo[3,2,1]octane, 2.2 g of colloid palladium and 165 ml of acetic acid is shaken at room temperature for 2 hours in a hydrogen atmosphere under atmospheric pressure. After the reaction is completed, the mixture is filtered to remove the catalyst. The filtrate is then evaporated to remove solvent. Water is added to the residue, and the aqueous mixture is made alkaline with ammonia. Then, the aqueous mixture is extracted with ether. The ether extract is dried and evaporated to remove solvent. 4.94 g of 1-(3-methoxyphenyl)-7-methyl-6-azabicyclo[3,2,-1]octane are obtained. Hydrochloride: M.p. 174°–176°C(recrystallized from a mixture of acetone, ethanol and ether).

b. A mixture of 5.22 g of 1-(3-methoxyphenyl)-7-methyl-6-azabicyclo[3,2,1]octane hydrochloride and 52 ml of 47% aqueous hydrobromic acid is refluxed for one hour under heating. After cooling, the crystalline precipitate is collected by filtration. The precipitate is recrystallized from a mixture of methanol and ether. 5.48 g of 1-(3-hydroxyphenyl)-7-methyl-6-azabicyclo[3,2,1]octane hydrobromide are obtained. M.p. 282°–284°C.

EXAMPLE 16

1-(3-hydroxyphenyl)-6-methyl-6-azabicyclo[3,2,1]octane

A mixture of 0.4 g of 1-(3-methoxyphenyl)-6-methyl-6-azabicyclo[3,2,1]octane hydrobromide and 4 ml of aqueous 48% hydrobromic acid is refluxed for 1.5 hours. After the reaction, the mixture is concentrated under reduced pressure. Aqueous ammonia is added to the residue, and the aqueous mixture is extracted with chloroform. The chloroform extract is washed with water, dried and then evaporated to remove solvent. The residue thus obtained is recrystallized from ethylacetate. 0.245 g of 1-(3-hydroxyphenyl)-6-methyl-6-azabicyclo[3,2,1]octane is obtained. M.p. 144.5°–145.5°C.

The following compounds are prepared in the same manner as described above:
(+)-1-(3-hydroxyphenyl)-6-methyl-6-azabicyclo[3,2,1]octane: M.p. 150°–152°C $[\alpha]_D^{23}$ + 19.5°(c = 0.37, 1N-HCl) (−)-1-(3-hydroxyphenyl)-6-methyl-6-azabicyclo[3,2,1]octane: M.p. 150°–152°C $[\alpha]_D^{23}$ −19.0°(c = 0.4, 1N-HCl)

EXAMPLE 17

1-(3-hydroxyphenyl)-6,7-dimethyl-6-azabicyclo[3,2,-1]octane

A mixture of 3.1 g of 1-(3-methoxyphenyl)-6,7-dimethyl-6-azabicyclo[3,2,1]octane hydrobromide and 30 ml of 48% aqueous hydrobromic acid is refluxed for 1.5 hours. After the reaction, the mixture is concentrated under reduced pressure. Aqueous ammonia is added to the residue, and the aqueous mixture is extracted with chloroform. The chloroform extract is washed with water, dried and then evaporated to remove solvent. The residue thus obtained is recrystallized from ethylacetate. 2.1 g of 1-(3-hydroxyphenyl)-6,7-dimethyl-6-azabicyclo[3,2,1]octane is obtained.

M.p. 182°–183°C.

Hydrobromide: M.p. 231°–234°C.

Hydrochloride: M.p. 238°–240°C(recrystallized from ethanol).

Sulfate: M.p. 192°–194°C(recrystallized from ethanol).

Methanesulfonate: M.p. 198°–199°C(recrystallized from ethanol).

Acetate: M.p 123°–125°C(recrystallized from acetone-ether).

Citrate: M.p. 161°–165°C(recrystallized from methanol).

Oxalate: M.p. 201°–202°C(decomp.)(recrystallized from methanol).

Maleate: M.p. 169°–170°C(recrystallized from methanol).

Fumarate: M.p. 227°–230°C(recrystallized from methanol).

Succinate: M.p. 152°–154°C(recrystallized from ethanol).

Phthalate: M.p. 136°–142°C(recrystallized from acetone-ether).

p-Toluenesulfonate: M.p. 168°–170°C(recrystallized from ethanol-ether).

Benzoate: M.p. 175 177°- C(recrystallized from methanol-ether).

The following compounds are prepared in the same manner as described above: (+)-1-(3-hydroxyphenyl)-6,7-dimethyl-6-azabicyclo[3,2,1]-octane: M.p. 152°–153°C. Hydrobromide: M.p 261°–263°C. $[\alpha]_D^{23} +$ 9.9°(c =0.79, water) Hydrochloride: M.p. 254°– 256°C. (−)-1-(3-hydroxyphenyl)-6,7-dimethyl-6-azabicyclo[3,2,1]octane: M.p. 152°–153°C. Hydrobromide: M.p. 261°–263°C. $[\alpha]_D^{23} -9.7°$(c = 0.79, water)

EXAMPLE 18

1-(3-hydroxyphenyl)-6-methyl-7-ethyl-6-azabicyclo[3,2,1]octane 1-(3-methoxyphenyl)-6-methyl-7-ethyl-6-azabicyclo[3,2,1]-octane is treated in the same manner as described in Example 16, whereby 1-(3-hydroxyphenyl)-6-methyl-7-ethyl-6-azabicyclo[3,2,1]octane is obtained. Yield 83.3% Hydrobromide: M.p. 245°–247°C.

EXAMPLE 19

1-(3-hydroxyphenyl)-6-benzyl-7-methyl-6-azabicyclo[3,2,1]octane

A mixture of 0.3 g of 1-(3-methoxyphenyl)-6-benzyl-7-methyl-6-azabicyclo[3,2,1]octane and 3 ml of 48% aqueous hydrobromic acid is refluxed for 30 minutes under heating. The mixture is concentrated under reduced pressure. Water is added to the residue, and the aqueous mixture is made alkaline with ammonia. Then, the aqueous mixture is extracted with chloroform. The chloroform extract is washed with water, dried and then evaporated to remove solvent. Methanolic hydrogen chloride is added to the residue in ether, and the crystalline precipitate is collected by filtration. The precipitate is recrystallized from ethanol. 0.22 g of 1-(3-hydroxyphenyl)-6-benzyl-7-methyl-6-azabicyclo[3,2,1]octane hydrochloride are obtained. M.p. 226°–230°C.

EXAMPLE 20

1-(3-hydroxyphenyl)-6-(3-benzoylpropyl)-6-azabicyclo[3,2,1]-octane

A mixture of 0.42 g of 1-(3-methoxyphenyl)-6-(3-benzoylpropyl)-6-azabicyclo[3,2,1]octane and 4 ml of 47% aqueous hydrobromic acid is refluxed for 45 minutes under heating. The mixture is concentrated under reduced pressure. The residue thus obtained is neutralized with aqueous ammonia and extracted with ether. The ether extract is dried and then evaporated to remove solvent. Then, methanolic hydrogen chloride is added to the residue in ether, and the precipitate is collected by filtration. 0.3 g of 1-(3-hydroxyphenyl)-6-(3-benzoylpropyl)-6-azabicyclo[3,2,1]octane hydrochloride is obtained as amorphous powder.

Infrared absorption spectrum: $\nu_{max.}^{chloroform}$(cm$^{-1}$): 3200(OH), 2300 –2800 NH$^+$); 1680(C=O); Mass Analysis: 349(M$^+$)

EXAMPLE 21

1-(3-hydroxyphenyl)-6-[3-(4-fluorobenzoyl)propyl]-6-azabicyclo[3,2,1]octane

A mixture of 0.5 g of 1-(3-methoxyphenyl)-6-[3-(4fluorobenzoyl)propyl]-6-azabicyclo[3,2,1]octane and 5 ml of 47% aqueous hydrobromic acid is refluxed for one hour. Then, the mixture is treated in the same manner as described in Example 20. 0.34 g of 1-(3-hydroxyphenyl)-6-[3-(4-fluorobenzoyl)propyl]-6-azabicyclo[3,2,1] octane hydrochloride is obtained as amorphous powder.

Infrared absorption spectrum: $\nu_{max.}^{chloroform}$ (cm$^{-1}$): 3200(OH), 2300–2800( NH$^+$), 1680(C=O); Mass Analysis: 367(M$^+$)

EXAMPLE 22

1-(3-hydrophenyl)-6,7-dimethyl-6-azabicyclo 3,2,1]octane

A mixture of 1.1 g of 1-(3-hydroxyphenyl)-7-methyl-6-azabicyclo[3,2,1]octane, 0.7 g of methyl iodide, 0.6 g of sodium bicarbonate and 10 ml of dimethylformamdie is stirred at 70° to 80°C for 2 hours. After cooling, water is added to the mixture, and the aqueous mixture is extracted with chloroform. The chloroform extract is washed with water, dried and then evaporated to remove solvent. Methanolic hydrogen chloride is added to the residue in ether, and the crystalline precipitate is collected by filtration. The precipitate is recrystallized from ethanol. 0.6 g of 1-(3-hydroxphenyl)6,7-dimethyl-6-azabicyclo[3,2,1,]octane hydrobromide are obtained. M.p 231°–233°C.

EXAMPLE 23

1-(3-hydroxyphenyl)-6,7-dimethyl-6-azabicyclo[3,2,-1]octane 0.37 g of 37% formelin is added to a soltuion of 0.5 g of 1-(3-hydroxyphenyl)-7-methyl-6-azabicyclo[3,2,-1]octane in 10 ml of ethanol. The solution is heated at 50°C for 30 minutes. After cooling, 0.3 g of sodium borohydride is added thereto. The mixture is stirred at room temperature for 2 hours. Then, the mixture is concentrated under reduced pressure. Water is added to the residue, and the aqueous mixture is extracted with a mixture of 50 ml of chloroform and 5 ml of ethanol. The chloroform-ethanol extract is dried and then evaporated to remove solvent. Methanolic hydrogen chloride is added to the residue in ether, and the crystalline precipitate is collected by filtration. The precipitate is recrystallized from ethanol. 0.2 g of 1-(3-hydroxyphenyl6,7-dimethyl-6-azabicyclo[3,2,1]octane hydrobromide is obtained. M.p. 231°–233°C.

EXAMPLE 24

1-(3-hydroxyphenyl)-6,7-dimethyl-6-azabicyclo[3,2,1]octane

A mixture of 0.3 g of 1-(3-hydroxyphenyl)-7-methyl-6-azabicyclo[3,2,1]octane and 10 ml of ethyl formate is refluxed for 4 hours under heating. The mixture is concentrated under reduced pressure. The residue is dissolved in 5 ml of tetrahydrofuran, and the tetrahydrofuran solution is added dropwise to 10 ml of tetrahydrofuran containing 0.3 g of lithium aluminium hydride. The mixture is refluxed for 2 hours under heating. Water is added to the mixture to decompose lithium aluminium hydride. Then, the aqueous mixture is acidified with 10% hydrochloric acid. After the aqueous mixture is made alkaline with ammonia, said mixture is extracted with a mixture of 50 ml of chloroform and 5 ml of methanol. The extract is dried and then evaporated to remove solvent. Methanolic hydrogen chloride is added to the residue in ether, and the crystalline precipitate is collected by filtration. The precipitate is recrystallized from ethanol. 0.16 g of 1-(3-hydroxyphenyl)-6,7-dimethyl-6-azabicyclo[3,2,1]octane hydrobromide is obtained. M.p. 231°–233°C.

EXAMPLE 25

1-(3-hydroxyphenyl)-6,7-dimethyl-6-azabicyclo[3,2,1]octane

A solution of 0.25 g of ethyl chloroformate in 5 ml of chloroform is added dropwise at 5° to 10°C to a mixture of 0.5 g of 1-(3-hydroxyphenyl)-7-methyl-6-azabicyclo[3,2,1]octane, 0.5 g of potassium carbonate and 20 ml of dimethylformamide. The mixture is stirred for 2 hours. Then, water is added to the mixture, and the aqueous mixture is extracted with chloroform. The chloroform extract is dried and then evaporated to remove solvent. The residue thus obtained is dissolved in 5 ml of tetrahydrofuran, and the tetrahydrofuran solution is added dropwise to 10 ml of tetrahydrofuran containing 0.4 g of lithium aluminium hydride. The mixture is refluxed for 3 hours under heating, and then treated in the same manner as described in Example 24. 0.28 g of 1-(3-hydrophenyl)-6,7-dimethyl-6-azabicyclo[3,2,1]octane hydrobromide is obtained. M.p. 231°–233°C.

EXAMPLE 26

1-(3-hydroxyphenyl)-6-ethyl-7-methyl-6-azabicyclo[3,2,1]octane

A mixture of 0.35 g of 1-(3-hydroxyphenyl)-7-methyl-6-azabicyclo[3,2,1]octane, 0.31 g of ethyl iodide, 0.31 g of sodium bicarbonate and 5 ml of dimethylformamide is stirred at 70° to 80°C for 2 hours. After cooling, water is added to the mixture, and the aqueous mixture is extracted with ether. The ether extract is washed with water, dried and then evaporated to remove solvent. Methanolic hydrogen chloride is added to the residue in ether, and the crystalline precipitate is collected by filtration. The precipitate is recrystallized from isopropanol. 0.38 g of 1-(3-hydroxyphenyl)-6-ethyl-7-methyl-6-azabicyclo[3,2,1]octane hydrochloride is obtained. M.p. 228°–231°C.

EXAMPLE 27

1-(3-hydroxyphenyl)-6-propyl-7-methyl-6-azabicyclo[3,2,1]octane

A mixture of 0.35 g of 1-(3-hydroxpehnyl)-7-methyl-6-azabicyclo[3,2,1]octane, 0.34 g of propyl iodide, 0.34 g of sodium bicarbonate and 5 ml of dimethylformamide is stirred at 70° to 80°C for 2 hours. After cooling, the mixture is treated in the same manner as described in Example 26. 0.32 g of 1-(3-hydroxyphenyl)-6-propyl-7-methyl-6-azabicyclo[3,2,1]octane hydrochloride is obtained. M.p. 244°–248°C.

EXAMPLE 28

1-(3-hydroxyphenyl)-6-cyclopropylmethyl-7-methyl-6-azabicyclo[3,2,1]octane

A mixture of 0.35 g of 1-(3-hydroxyphenyl)-7-methyl-6-azabicyclo[3,2,1]octane, 0.23 g of cyclopropylmethyl bromide, 0.2 g of sodium bicarbonate and 5 ml of dimethylformamide is stirred at 70° to 80°C for 2 hours. After cooling, the mixture is treated in the same manner as described in Example 26. 0.3 g of 1-(3-hydroxyphenyl)-6-cyclopropylmethyl-7-methyl-6-azabicyclo[3,2,1]octane hydrochloride are obtained. M.p. 216°–219°C(recrystallized from a mixture of ethanol and ether).

EXAMPLE 29

1-(3-hydroxyphenyl)-6-n-amyl-7-methyl-6-azabicyclo[3,2,1]octane

A mixture of 0.35 g of 1-(3-hydroxyphenyl)-7-methyl-6-azabicyclo[3,2,1]octane, 0.3 g of n-amyl bromide, 0.3 g of sodium bicarbonate and 5 ml of dimethylformamide is stirred at 100°C for 2 hours. After cooling, the mixture is treated in the same manner as described in Example 26. 0.39 g of 1-(3-hydroxyphenyl)-6-n-amyl-7-methyl-6-azabicyclo[3,2,1]octane hydrochloride is obtained. M.p. 151°–154°C(recrystallized from acetone).

EXAMPLE 30

1-(3-hydroxyphenyl)-6-n-hexyl-7-methyl-6-azabicyclo[3,2,1]octane

A mixture of 0.35 g of 1-(3-hydroxyphenyl)-7-methyl6-azabicyclo[3,2,1]octane, 0.32 g of n-hexyl bromide, 0.17 g of sodium bicarbonate and 5 ml of dimethylformamide is stirred at 70° to 80°C for 2 hours. After cooling, the mixture is treated im the same manner as described in Example 26. 0.5 g of 1-(3-hydroxyphenyl)-6-n-hexyl-7-methyl-6-azabicyclo[3,2, 1]octane hydrochloride are obtained. M.p. 164°–165°C(recrystallized from ethanol).

EXAMPLE 31

1-(3-hydroxyphenyl)-6-n-hexyl-6-azabicyclo[3,2,1]octane 0.73 g of n-caproyl chloride is added to a mixture of 0.5 g of 1-(3-hydroxyphenyl)-6-azabicyclo[3,2,1]octane, 0.62 g of triethylamine and 10 ml of dimethylformamide. The mixture is stirred at room temperature for 4 hours. Then, water is added to the mixture, and the aqueous mixture is extracted with chloroform. The chloroform extract is washed with water, dried and then evaporated to remove solvent. The residue thus obtained is dissolved in 40 ml of tetrahydrofuran. 0.9 g of lithium aluminium hydride is added to the solution, and the solution is refluxed for 12 hours under heating. After cooling, water is added to the reaction solution to decompose lithium aluminium hydride. The reaction solution is acidified with hydrochloric acid. Then, the reaction solution is made alkaline with aqueous ammonia and extracted with chloroform. The chloroform extract is washed with water, dried and then evaporated to remove solvent. The residue is dissolved in 5 ml of chloroform. The chloroform solution is poured onto the column of 50 g of silica gel. Then, the column is eluted with a mixture of 950 ml of chloroform and 50 ml of methanol, and the effluent is evaporated to remove solvent. The residue thus obtained is distilled under reduced pressure, whereby 0.48 g of 1-(3-hydroxyphenyl)-6-n-hexyl-6-azabicyclo[3,2,1]octane is obtained as a viscous oil boiling at 250°C(bath temperature/0.1 mmHg.

EXAMPLE 32

1-(3-hydroxyphenyl)-6-cyclobutylmethyl-6-azabicyclo[3,2,1]octane 0.52 g of cyclobutylcarbonyl chloride is added to a mixture of 0.43 g of 1-(3-hydroxyphenyl)-6-azabicyclo[3,2,1]octane, 0.51 g of triethylamine and 8 ml of dimethylformamide. The mixture is stirred at room temperature for 15 hours. Then, water is added to the mixture, and the aqueous mixture is extracted with chloroform. The chloroform extract is washed with water, dried and then evaporated to remove solvent. The residue thus obtained is dissolved in 25 ml of tetrahydrofuran. 0.6 g of lithium aluminium hydride is added to the solution, and the solution is refluxed for 3 hours under heating. After cooling, water is added to the reaction solution to decompose lithium aluminium hydride. The reaction solution is acidified with hydrochloric acid. Then, the reaction solution is made alkaline with aqueous ammonia and extracted with chloroform. The chloroform extract is washed with water, dried and then evaporated to remove solvent. The residue is dissolved in 5 ml of chloroform. The chloroform solution is poured onto the column of 30 g of silica gel. Then, the column is eluted with a mixture of 500 ml of chloroform and 25 ml of methanol, and the effluent is evaporated to remove solvent. The residue thus obtained is distilled under reduced pressure, whereby 0.42 g of 1-(3-hydroxyphenyl)-6-cyclobutylmethyl-6-azabicyclo[3,2,1]octane is obtained as an viscous oil boiling at 240°C(bath temperature)/0.1 mmHg.

EXAMPLE 33

1-(3-hydroxyphenyl)-6-phenethyl-7-methyl-6-azabicyclo[3,2,1]octane 0.62 g of phenylacetyl chloride is added dropwise under ice-cooling to a mixture of 0.35 g of 1-(3-hydroxyphenyl)7-methyl-6-azabicyclo[3,2,1]octane, 1 ml of triethylamine and 7 ml of methylenedichloride. The mixture is stirred at room temperature for 20 hours. Then, the mixture is concentrated under reduced pressure. Water is added to the residue, and the aqueous mixture is extracted with benzene. The benzene extract is washed with diluted hydrochloric acid, water, aqueous sodium bicarbonate and water, successively. The benzene extract is dried and evaporated to remove solvent. The residue thus obtained is dissolved in 12 ml of tetrahydrofuran. 0.6 g of lithium aluminium hydride is added to the tetrahydrofuran solution, and said solution is refluxed for 1.5 hours. After cooling, diluted hydrochloric acid is added to the reaction solution to decompose lithium aluminium hydride. Then, the reaction solution is made alkaline with aqueous ammonia and extracted with chloroform. The chloroform extract is washed with water, dried and then evaporated to remove solvent. The residue is dissolved in 5 ml of chloroform. The chloroform solution is poured onto a column of 20 g of silica gel. Then, the column is eluted with a mixture of 300 ml of chloroform and 50 ml of methanol, and the effluent is evaporated to remove solvent. Methanolic hydrogen chloride is added to the residue in ether, and the crystalline precipitate is collected by filtration. The precipitate is recrystallized from acetone. 0.09 g of 1-(3-hydroxyphenyl)-6-phenethyl- 7-methyl-6-azabicyclo[3,2,1]octane hydrochloride is obtained. M.p. 231°–233°C.

EXAMPLE 34

1-(3-hydroxyphenyl)-6-(2-benzoylethyl)-6-azabicyclo[3,2,1]octane

A mixture of 0.4 g of 1-(3-hydroxyphenyl)-6-azabicyclo[3,2,1]octane, 0.4 g of 2-benzoylethyl chloride, 0.4 of potassium carbonate, 0.03 g of potassium iodide and 5 ml of dimethylformamide is stirred at 100°C for 4 hours in a nitrogen atmosphere. After cooling, water is added to the mixture, and the aqueous mixture is extracted with chloroform. The chloroform extract is washed with water, dried and then evaporated to remove solvent. The residue thus obtained is dissolved in 5 ml of chloroform. The chloroform solution is poured onto a column of 40 g of silica gel. Then, the column is eluted with a mixture of 300 ml of chloroform and 15 ml of methanol, and the effluent is evaporated to remove solvent. Methanolic hydrogen chloride is added to the residue in ether, and the crystalline precipitate is collected by filtration. The precipitate is recrystallized from a mixture of methanol and ether. 0.1 g of 1-(3-hydroxyphenyl)-6-(2-benzoylethyl)-6-azabicyclo[ 3,2,1]octane hydrochloride is obtained. M.p. 187°–189°C.

EXAMPLE 35

1-(3-hydroxyphenyl)-6-(2-benzoylethyl)-6-azabicyclo[3,2,1]octane

A mixture of 0.4 g of 1-(3-hydroxyphenyl)-6-azabicyclo[3,2,1]octane, 0.69 g of N-(2-benzoylethyl)-N,N,N-trimethylammonium iodide, 0.24 g of potassium carbonate and 5 ml of dimethylformamide is stirred at room temperature in a nitrogen atmosphere for 5 hours. After the reaction, water is added to the mixture, and the aqueous mixture is extracted with ether. The ether extract is dried and then evaporated to remove solvent. Methanolic hydrogen chloride is added to the residue in ether, and the crystalline precipitate is collected by filtration. The precipitate is recrystallized from a mixture of methanol and ether. 0.64 g of 1-(3-hydroxyphenyl)-6-(2-benzoylethyl)-6-azabicyclo[3,2,-1]octane hydrochloride is obtained. M.p. 187°–189°C.

EXAMPLE 36

1-(3-acetyloxyphenyl(-6,7-dimethyl-6-azabicyclo[3,2,-1]octane

A mixture of 0.5 g of 1-(3-hydroxyphenyl)-6,7-dimethyl-6-azabicyclo[3,2,1]octane hydrobromide, 10 ml of acetic acid anhydride and 0.3 g of potassium acetate is heated for one hour on a water bath. After the reaction, the mixture is concentrated under reduced pressure. Ether and water are added to the residue, and the aqueous mixture is made alkaline with 5 % aqueous sodium bicarbonate. The aqueous mixture is extracted with ether. The ether extract is washed with water, dried and then evaporated to remove solvent. Methanolic hydrogen chloride is added to the residue in ether, and the crystalline precipitate is collected by filtration. The precipitate is recrystallized from a mixture of ethanol and ether. 0.37 g of 1-(3-acetyloxyphenyl)-6,7-dimethyl-6-azabicyclo[3,2,1]octane hydrochloride is obtained. M.p. 250°–252°C.

The following compounds are prepared in the same manner as described above:

(+)-1-(3-acetyloxyphenyl)-6,7-dimethyl-6-azabicyclo[3,2,1]octane hydrochloride: M.p. 207°–211°c. $[\alpha]_D^{24}$ + 9.9°(c = 0.45, methanol)

(−)-1-(3-acetyloxyphenyl)-6,7-dimethyl-6-azabicyclo[3,2,1]octane hydrochloride: M.p. 208°–210°C. $[\alpha]_D^{24}$ −9.9°(c = 0.38, methanol)

EXAMPLE 37

1-(3-acetyloxyphenyl)-6-methyl-7-ethyl-6-azabicyclo[3,2,1]octane 1-(3-hydroxyphenyl)-6-methyl-7-ethyl-6-azabicyclo[3,2,1]octane is treated in the same manner as described in Example 36, whereby 1-(3-acetyloxyphenyl)-6-methyl-7-ethyl-6-azabicyclo [3,2,1]octane hydrobromide is obtained. Yield: 65 % M.p. 237°–240°C.

EXAMPLE 38

1-(3-propionyloxyphenyl)-6,7-dimethyl-6-azabicyclo[3,2,1]octane

A mixture of 0.25 g of 1-(3-hydroxyphenyl)-6,7-dimethyl-6-azabicyclo[3,2,1]octane hydrobromide, 5 ml of propionic acid anhydride and 0.3 ml of pyridine is heated at 80° to 90°C for 2 hours. After cooling, the crystalline precipitate is collected by filtration, washed with acetone, and then recrystallized from a mixture of chloroform and ether. 0.25 g of 1-(3-propionyloxyphenyl)-6,7-dimethyl-6-azabicyclo[3,2,1]octane hydrobromide is obtained. M.p. 226°–228°C.

EXAMPLE 39

1-(3-n-hexanoyloxyphenyl)-6,7-dimethyl-6-azabicyclo[3,2,1]octane

A mixture of 0.25 g of 1-(3-hydroxyphenyl)-6,7-dimethyl-6-azabicyclo[3,2,1]octane hydrobromide, 8 ml of n-hexanoic acid anhydride and 0.1 ml of pyridine is heated at 120°C for 3 hours. After the reaction, the mixture is concentrated under reduced pressure. Ether is added to the residue, and the crystalline precipitate is collected by filtration. The precipitate is recrystallized from a mixture of chloroform and ether. 0.155 g of 1-(3-n-hexanoyloxyphenyl)6,7 -dimethyl-6-azabicyclo[3,2,1]octane hydrobromide is obtained. M.p. 95°–97°C.

EXAMPLE 40

1-(3-benzoyloxyphenyl)-6,7-dimethyl-6-azabicyclo[3,2,1]octane 0.35 g of 1-(3-hydroxyphenyl)-6,7-dimethyl-6-azabicyclo [3,2,1]octane is dissolved in 4 ml of pyridine, and a solution of 0.28 g of benzoyl chloride in 2 ml of benzene is added thereto under ice-cooling. The mixture is stirred for 45 minutes. Then, the mixture is concentrated under reduced pressure. The residue thus obtained is washed with ether and then recrystallized from a mixture of ethylacetate and acetone. 0.43 g of 1-(3-benzoyloxyphenyl)-6,7-dimethyl-6-azabicyclo[3,2,1]octane hydrochloride is obtained. M.p. 207°–209°C.

EXAMPLE 41

1-(3-nicotinoyloxyphenyl)-6,7-dimethyl-6-azabicyclo[3,2,1]octane

To a solution of 0.231 g of 1-(3-hydroxyphenyl)-6,7-dimethyl-6-azabicyclo[3,2,1]octane in 4 ml of pyridine is added 0.376 g of nicotinoyl chloride hydrochloride under icecooling. The solution is stirred at room temperature overnight. Then, the solution is concentrated under reduced pressure. The resudue thus obtained is washed with ether, and then recrystallized from a mixture of ethanol, acetone and ether. 0.17 g of 1-(3-nicotinoyloxyphenyl)-6,7-dimethyl-6-azabicyclo[3,2,-1]octane dihydrochloride hemihydrate is obtained. M.p. 210°–218°C.

What we claim is:

1. A compound of the formula:

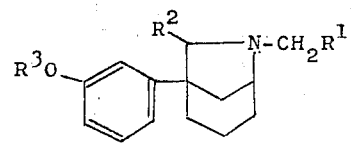

wherein $R^1$ is hydrogen, phenyl, alkyl of one to five carbon atoms, cycloalkyl of three to four carbon atoms, or alkyl of one to five carbon atoms having a substituent selected from the group consisting of phenyl, benzoyl and 4-fluorobenzoyl, $R^2$ is hydrogen or alkyl of one to three carbon atoms, and $R^3$ is hydrogen, alkanoyl of two to six carbon atoms, benzoyl or nicotinoyl, or a pharmaceutically acceptable acid addition salt thereof.

2. The compound as claimed in claim 1, wherein $R^1$ is selected from the group consisting of hydrogen, methyl, ethyl, butyl, amyl, cyclopropyl, cyclobutyl, phenyl, benzyl, benzoylmethyl, 2-benzoylethyl and 2-(4-fluorobenzoyl)ethyl, $R^2$ is hydrogen, methyl or ethyl, and $R^3$ is selected from the group consisting of hydrogen, acetyl, propionyl, hexanoyl, benzoyl and nicotinoyl.

3. The compound as claimed in claim 1, wherein $R^1$ is selected from the group consisting of hydrogen, nbutyl, n-amyl, cyclopropyl, benzyl, 2-benzoylethyl and 2-(4-fluorobenzoyl)ethyl, $R^2$ is hydrogen or methyl, and $R^3$ is selected from the group consisting of hydrogen, acetyl, propionyl, benzoyl and nicotinoyl.

4. The compound as claimed in claim 3, wherein each of $R^1$, $R^2$ and $R^3$ is hydrogen.

5. The compound as claimed in claim 3, wherein each of $R^1$ and $R^3$ is hydrogen, and $R^2$ is methyl.

6. The compound as claimed in claim 3, wherein $R^1$ is n-butyl, $R^2$ is methyl, and $R^3$ is hydrogen.

7. The compound as claimed in claim 3, wherein $R^1$ is n-amyl, $R^2$ is methyl, and $R^3$ is hydrogen.

8. The compound as claimed in claim 3, wherein $R^1$ is cyclopropyl, $R^2$ is methyl, and $R^3$ is hydrogen.

9. The compound as claimed in claim 3, wherein $R^1$ is benzyl, $R^2$ is methyl, and $R^3$ is hydrogen.

10. The compound as claimed in claim 3, wherein $R^1$ is 2-benzoylethyl, and each of $R^2$ and $R^3$ is hydrogen.

11. The compound as claimed in claim 3, wherein $R^1$ is 2-(4-fluorobenzoyl)ethyl, and each of $R^2$ and $R^3$ is hydrogen.

12. The compound as claimed in claim 3, wherein $R^1$ is hydrogen, $R^2$ is methyl, and $R^3$ is acetyl.

13. The compound as claimed in claim 3, wherein $R^1$ is hydrogen, $R^2$ is methyl, and $R^3$ is propionyl.

14. The compound as claimed in claim 3, wherein $R^1$ is hydrogen, $R^2$ is methyl, and $R^3$ is benzoyl.

15. The compound as claimed in claim 3, wherein $R^1$ is hydrogen, $R^2$ is methyl, and $R^3$ is nicotinoyl.

16. The compound as claimed in claim 1, wherein said compound is an optically active (+)-isomer.

17. The compound as claimed in claim 2, wherein said compound is an optically active (+)-isomer.

18. The compound as claimed in claim 3, wherein said compound is an optically active (+)-isomer.

19. The compound as claimed in claim 4, wherein said compound is an optically active (+)-isomer.

20. The compound as claimed in claim 5, wherein said compound is an optically active (+)-isomer.

21. A compound according to claim 1 wherein $R^3$ is hydrogen.

22. A compound according to claim 21 wherein $R^1$ is hydrogen, n-butyl, n-amyl, cyclopropyl, benzyl, 2-benzoylethyl, 2-(4-fluorobenzoyl)-ethyl and $R^2$ is hydrogen or methyl.

23. A compound according to claim 21 wherein said compound is an optically active (+) isomer.

24. A compound according to claim 22 wherein said compound is an optically active (+) isomer.

* * * * *